United States Patent [19]

Himmelmann

[11] 4,061,499
[45] Dec. 6, 1977

[54] PROCESS FOR HARDENING SILVER HALIDE PHOTOGRAPHIC LAYERS WITH ORGANIC ASYMMETRIC MONOCARBODIIMIDES

[75] Inventor: Wolfgang Himmelmann, Leverkusen, Germany

[73] Assignee: AGFA-Gevaert Aktiengesellschaft, Leverkusen, Germany

[21] Appl. No.: 730,263

[22] Filed: Oct. 6, 1976

[30] Foreign Application Priority Data

Oct. 11, 1975    Germany .............................. 2545755

[51] Int. Cl.$^2$ ................................................ G03C 1/30
[52] U.S. Cl. .......................................... 96/111; 96/67; 96/77; 96/50 PT; 106/125; 260/112 R; 260/117; 427/338
[58] Field of Search ................. 96/111, 50 PT, 67, 77; 260/117, 112; 106/125; 427/338

[56] References Cited

U.S. PATENT DOCUMENTS

| 3,100,704 | 8/1963 | Coles et al. ............................. 96/111 |
| 3,880,665 | 4/1975 | Himmelmann ........................ 96/111 |

OTHER PUBLICATIONS

Oftedah, et al.: Photographic Emulsions for Obtaining Magenta Images, Chem. Abstracts, vol. 75, 1971, 28259p.

Primary Examiner—Won H. Louie, Jr.
Attorney, Agent, or Firm—Connolly and Hutz

[57] ABSTRACT

As quick-acting hardeners for protein-containing photographic layers water-soluble, organic, asymmetric monocarbodiimides containing an alkyl ammonium group and having a carbonamide group attached to the nitrogen atom are used.

9 Claims, No Drawings

PROCESS FOR HARDENING SILVER HALIDE PHOTOGRAPHIC LAYERS WITH ORGANIC ASYMMETRIC MONOCARBODIIMIDES

This invention relates to a process for hardening photographic layers which contain protein, preferably gelatine.

Numerous substances have already been described as hardeners for proteins and in particular for gelatine. These include, for example, metal salts such as chromium, aluminium or zirconium salts, aldehydes and halogenated aldehyde compounds, in particular formaldehyde, dialdehydes and mucochloric acid, 1,2- and 1,4-diketones such as cyclohexane 1,2-dione and quinones as well as chlorides of dibasic organic acids, the anhydrides of tetracarboxylic acids, compounds containing several reactive vinyl groups such as vinyl sulphones, acrylamides, compounds containing at least two 3-membered heterocyclic rings which are easily split open such as ethylene oxide and ethyleneimine, polyfunctional methane sulphonic acid esters and bis-α-chloroacylamide compounds.

High molecular weight hardeners, such as polyacrolein and its derivatives or copolymers and alginic acid derivatives, have recently become known. These are used mainly as hardeners confined to the layer in which they are contained.

The use of the above mentioned compounds for photographic purposes have numerous serious disadvantages. Some of the compounds are photographically active and therefore unsuitable as hardeners for photographic materials while others have such a deleterious effect on the physical properties of gelatine layers, such as their brittleness, that they cannot be used. Others again cause discolorations or a change in pH during the hardening reaction. Moreover, when hardening photographic layers it is particularly important that the degree of hardening should reach its maximum as soon as possible after drying so that the permeability of the photographic material to developer solution will not constantly change as is the case, for example, when mucochloric acid or formaldehyde is used as a hardener.

Some cross-linking agents for gelatine, for example ethyleneimine compounds, also have a damaging effect on the skin so that their use is contraindicated on physiological grounds.

The use of trichlorotriazine, hydroxydichlorotriazine and dichloraminotriazines as hardeners is also known. These compounds have the disadvantages of a relatively high vapour pressure, precipitation of hydrochloric acid during the hardening reaction and a harmful physiological action. Water-soluble derivatives which contain carboxyl and sulphonic acid groups and which are obtained by reacting cyanuric chloride with 1 mol of a diaminoalkyl or diaminoaryl sulphonic acid or carboxylic acid do not have these disadvantages and have therefore recently been proposed as hardeners. Their use in practice is, however, limited owing to their high solubility which causes them to decompose when left to stand in aqueous solutions so that they rapidly lose their activity.

Finally, when choosing a hardener for photographic layers containing gelatine it is most important both in the preparation of the layers and in processing them, that it should be possible to predetermine the onset of the cross-linking reaction within certain limits, for example by choice of the drying temperature or of the pH.

Compounds having two or more acrylic acid amido or vinylsulphone groups in the molecule are also known as hardeners for photographic gelatine layers, for example divinylsulphone, arylene-bis-vinylsulphones, N,N', N''-trisacryloylhydrotriazine or methylene-bis-vinylsulphonamide.

Although a satisfactory hardening action is obtained with these compounds after a certain time, the compounds are only sparingly soluble in water so that hardening is liable to be non-uniform within the layer.

The consequences of the undesirable properties of the known hardeners indicated above are extremely important from a photographic point of view since important photographic properties, such as the gradation and sensitivity and in many cases also the silver covering powder, depend on the degree of cross-linkage of the layer-forming colloid and constantly change in the course of storage. Although this disadvantage can be attenuated by a brief after-treatment of the solidified layer with ammonia or an amine, it cannot be completely overcome by this method. Added to this is the disadvantage that aliphatic divinylsulphones have a damaging effect on the skin.

For a long time now carbodiimides have also been known as hardeners for photographic materials. Non-ionic carbodiimides have been described as hardeners for photographic proteins in DL-PS 7218. The iodides of carbodiimides which contain amino groups have been disclosed in DT-PS 1,148,446 and toluene and methylsulphonates in U.S. Pat. No. 3,100,704. Combinations of polymers containing carboxylic acid with gelatine and carbodiimides have been disclosed in GB-PS 1,275,587. Hardening of gelatine with 1-ethyl-3-dimethylaminopropylcarbodiimide hydrochloride has been described in the publication by Robinson, in Journal of Photographic Science, Vol. 16 (1968) page 41.

Carbodiimide compounds are reasonably suitable as rapid hardeners but they do have photographic and toxicological disadvantages. Non-ionic carbodiimides such as dicyclohexyl carbodiimide or diisopropylcarbodiimide are difficult to dissolve and have an irritant effect on the skin. The urea compounds produced in the reaction precipitate in the layer and cause cloudiness. Moreover, the simpler carbodiimides are known to be allergens. Carbodiimides must be made water-soluble before they can be used by introducing amino groups. Compounds containing amino groups are photographically active and still physiologically active. They reduce the sensitivity after storage and increase photographic fogging in colour photographic emulsions which contain emulsified colour couplers. Lastly, water-soluble carbodiimides containing amino groups react with phenolic cyan colour components, thereby reducing the final density values.

It is well known that carbodiimides react with phenols and thereby inhibit the coupling reaction in cyan colour components (F. Kurzer and K. Douraghi-Zadeh, Chem. Reviews, Vol. 67, No. 2, page 118 (1967)).

It is an object of the present invention to provide quick-acting hardeners for protein-containing photographic layers, in particular for gelatine-containing colour photographic layers, which have no harmful physiological action, which have no deleterious effect on the sensitisers and colour components contained in photographic materials, and which maintain their activity over several hours in dilute gelatine solutions and dilute cellulose sulphate solutions.

The present invention relates to a process for hardening photographic layers containing protein, in particular gelatine, characterised in that the hardener used is a water-soluble, organic, asymmetric monocarbodiimide containing an alkyl ammonium group and having a carbonamide group attached to the nitrogen atom.

The carbodiimides used according to the invention preferably correspond to the following general formula:

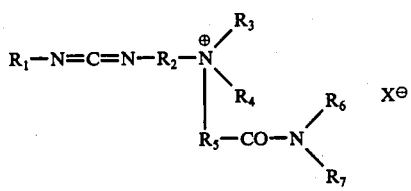

wherein
$R_1$ denotes alkyl with 1 to 6 carbon atoms, cycloalkyl such as cyclohexyl, aralkyl such as

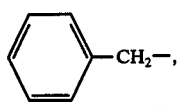

alkoxyalkyl such as methoxyethyl or an olefinically unsaturated lower aliphatic hydrocarbon group such as allyl, denotes alkylene with 2 to 4 carbon atoms, $R_3$ and $R_4$ denote alkyl with 1 to 3 carbon atoms or $R_3$ and $R_4$ together denote the atoms required for completing a 5- to 7-membered saturated heterocyclic ring which in addition to the nitrogen atom may contain other heteroatoms such as oxygen, for example pyrrolidine, piperidine, perhydroazepine or morpholine, $R_5$ denotes alkylene with 1 to 3 carbon atoms, $R_6$ denotes hydrogen, alkyl with 1 to 4 carbon atoms, cycloalkyl such as cyclohexyl, an optionally substituted aryl group such as phenyl or tolyl, or $SO_2$-alkyl such as $SO_2CH_3$, $R_7$ denotes hydrogen or alkyl with 1 to 8 carbon atoms, or $R_6$ and $R_7$ together denote the atoms required for completing a 5- to 7-membered saturated heterocyclic ring which may contain other hetero atoms in addition to nitrogen, such as oxygen, for example pyrrolidine, piperidine, perhydroazepine or morpholine, and $X^-$ denotes an anion such as Cl' or Br'.

The following compounds are examples of preferred representatives of the carbodiimides according to the invention:

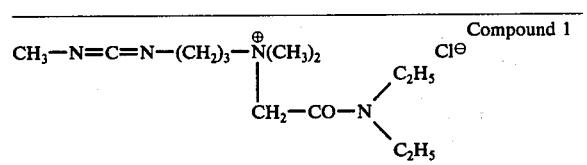

Compound 1

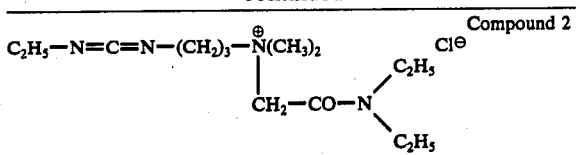

Compound 2

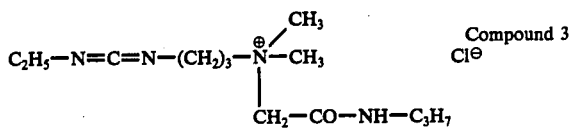

Compound 3

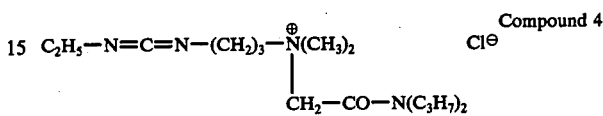

Compound 4

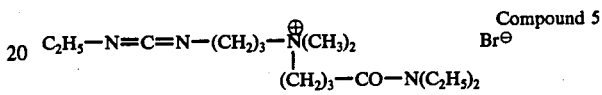

Compound 5

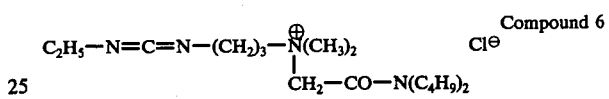

Compound 6

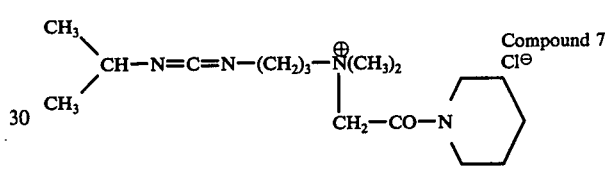

Compound 7

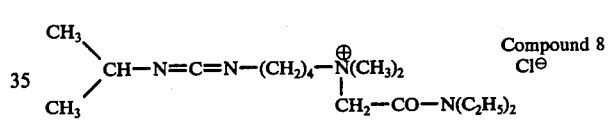

Compound 8

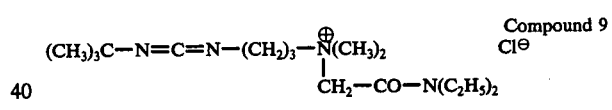

Compound 9

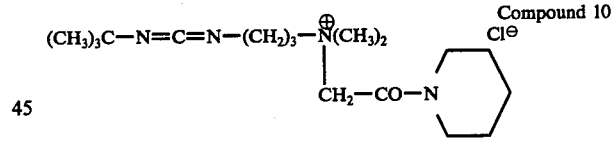

Compound 10

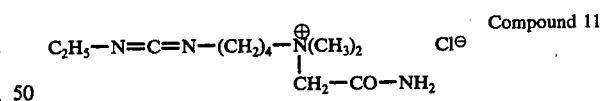

Compound 11

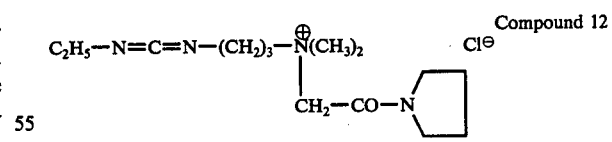

Compound 12

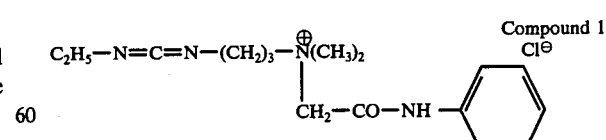

Compound 13

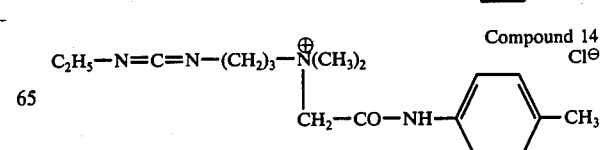

Compound 14

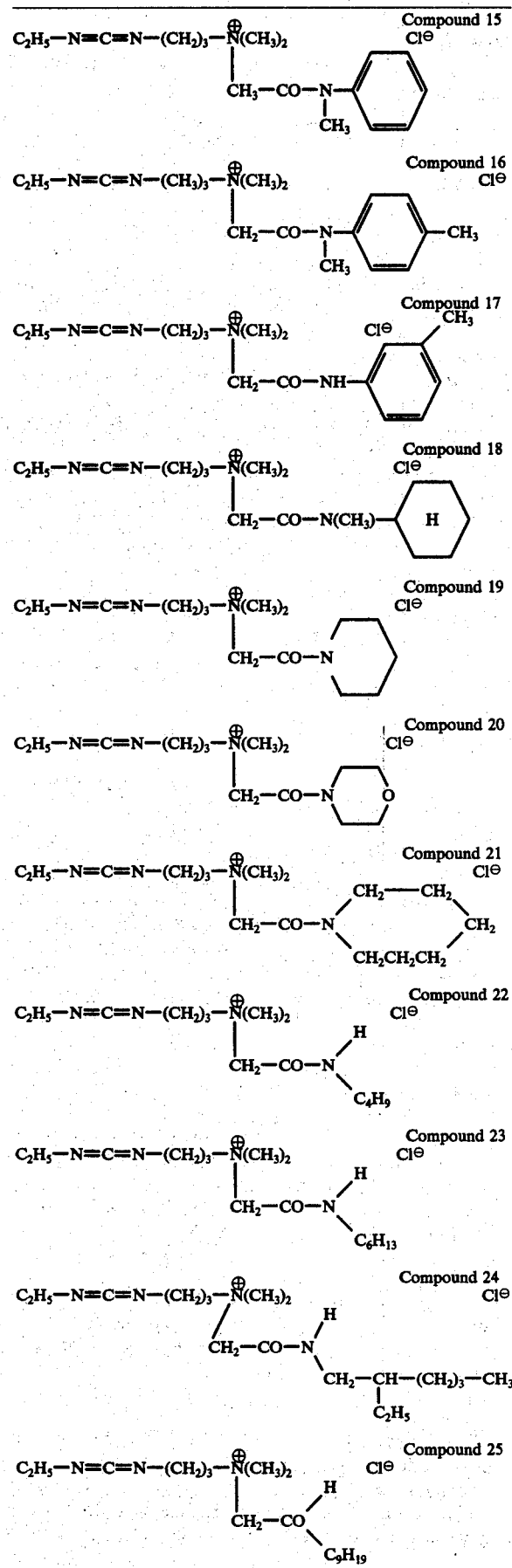
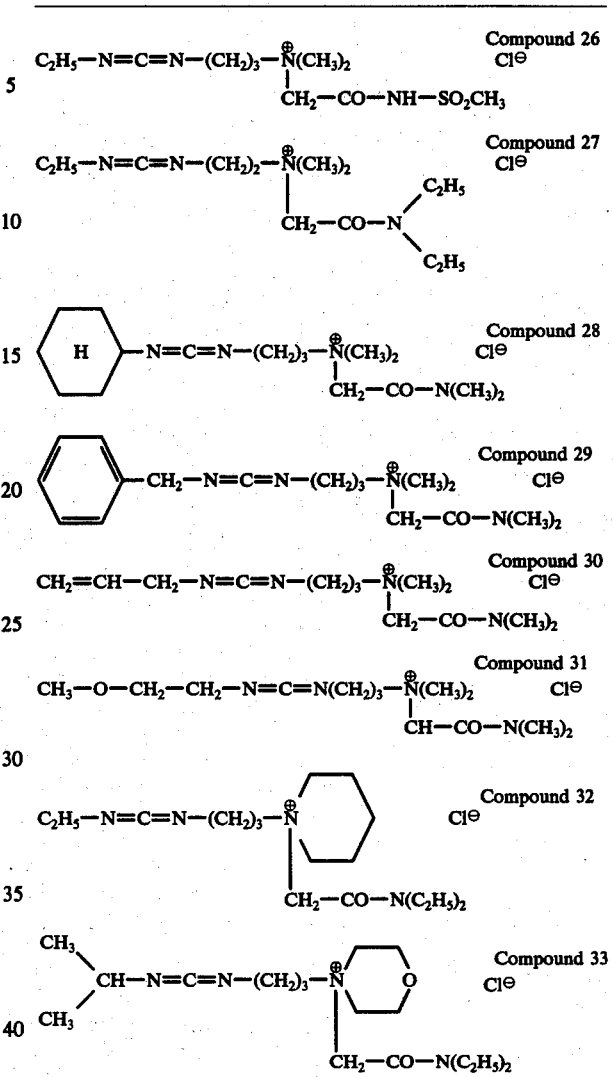

The compounds can easily be prepared from carbodiimides containing amino groups by reacting them with ester carbonamides, halogen alkyl carbonamides or alkyl or aryl sulphonic acid esters of hydroxyalkyl carbonamides. The preparation of carbodiimides containing amino groups of the formula R-N=C=N-$(CH_2)_3$-N$(CH_3)_2$ used as starting materials has been described by Sheehan et al in J. Org. Chem. 26, page 2525 (1961).

All other derivatives used as starting materials can be obtained very simply by this method, using the correspondingly substituted amines. Various starting compounds are also commercially available, e.g. 1-ethyl-3-dimethylaminopropyl-carbodiimide (OTT, Chem. Company Muskegon, Michigan U.S.A. or Ega-Chemie KG, Federal Republic of Germany). Preparation of the compounds has also been described in U.S. Patent Nos. 2,938,892 and 3,135,748.

The process of preparing the compounds will now be explained with the aid of the following Examples. Preparation of Compound 2:

30 g of chloroacetyl-N,N-diethylamide are dissolved in 100 ml of absolute acetone. 30.1 g of 1-ethyl-3-(3-dimethylaminopropyl)-carbodiimide are added to the mixture. The reaction is completed within 2 hours at 35° to 40° C. The solvent is removed under vacuum and the residue is triturated repeatedly with absolute ether. The product is then dried in a desiccator.

Yield: 54 g Melting point: 94° to 95° C.

| Analysis: | Found | Theoretical |
|---|---|---|
| C | 54.5% | 55.2% |
| H | 9.4 | 9.5 |
| O | 5.7 | 5.2 |
| N | 17.8 | 18.4 |
| Cl | 11.7 | 11.7 |

Preparation of Compound 19

32.4 g of N-chloroacetylpiperidide are reacted with 30.1 g of 1-ethyl-3-(3-dimethylaminopropyl)-carbodiimide in 100 ml of acetone as described above.

The mixture is left to stand at 35° to 40° C for 7 hours. The residue crystallises after removal of the solvent. Triturating the residue with absolute ether and drying yields the compound with a melting point of 114° C.

Yield: 50 g.

Preparation of Compound 4

35.4 g of chloroacetyl-N,N-dipropylamide are reacted as described for compound 2. 46 g of compound having a melting point of 76° to 77° C are obtained.

The carbodiimides used according to the invention which contained ammonium-carbonamide groups are eminently suitable for use as hardeners for gelatine layers of the kind which contain additives emulsified in hydrophobic water-soluble droplets. The carbodiimides are not only hydrophilic but also strongly polar and therefore cannot migrate into the lipophilic particles.

Owing to their ammonium carbonamide structure, the carbodiimides used according to the invention have practically no vapour pressure at room temperature. They are not steam volatile and do not migrate into the drying air. They can therefore be handled without health risk to the operator. The structure moreover ensures that the hardener remains in the aqueous phase (gelatine phase) at all pH values. The carbodiimides used according to the invention differ in this respect from all previously known basic carbodiimides such as 1-ethyl-3-(3-dimethylaminopropyl)-carbodiimide.

The compounds used according to the invention are preferably added to the protein layers which are to be hardened immediately before the layers are cast, preferably in the form of aqueous or alcoholic or aqueous-alcoholic solutions. It is necessary to add the compounds shortly before casting because they react very rapidly with gelatine or other proteins commonly used in photography. Once the compounds have been added, the casting solutions should be cast within a few minutes. The speed of the hardening reaction depends mainly on the concentration of the proteins in the casting solution.

Another possible method of using the hardening compounds is to cast the casting solutions before they have been hardened and then coat the resulting layers with a solution of the hardening compounds. Alternatively, the photographic materials may be bathed in aqueous, sodium sulphate-containing solutions of the compounds in the course of the photographic process. For example, unhardened or only slightly hardened photographic layers may be bathed in such solutions before development.

The expression "photographic layers" in this context means any layers in general used as photographic materials, for example light-sensitive silver halide emulsion layers, protective layers, filter layers, antihalation layers, backing layers or photographic auxiliary layers in general.

Light-sensitive emulsion layers for which the hardening process according to the invention is particularly suitable include, for example, layers based on unsensitised emulsions, orthochromatic, panchromatic or infrared emulsions, X-ray emulsions and other spectrally sensitised emulsions. The hardening process according to the invention has also proved to be suitable for hardening gelatine layers used for various black-and-white and colour photographic processes such as negative, positive and diffusion transfer processes or printing processes. The process according to the invention has been found to be particularly suitable for hardening photographic layer combinations used for carrying out colour photograhic processes, e.g. those containing emulsion layers with colour couplers or emulsion layers intended to be treated with solutions which contain colour couplers.

The effect of the compounds used according to the invention is not impaired by the usual photographic additives. Moreover, the hardeners are inert towards photographically active substances such as water-soluble and emulsified water-insoluble colour components, stabilizers, or sensitisers. They also have no deleterious effect on light-sensitive silver halide emulsions. Furthermore, the compounds may be combined with any of the compounds belonging to the previously known classes of hardeners, for example with formalin, mucochloric acid, triacryloformal, bisvinylsulphones, bisvinylsulphonamides, dialdehydes or bischloroacetamides.

The emulsion layers may contain as light-sensitive components any known silver halides such as silver chloride, silver iodide, silver bromide, silver iodobromide, silver chlorobromide or silver chloroiodobromide. The emulsions may be chemically sensitised with noble metal compounds, e.g. compounds of ruthenium, rhodium, palladium, iridium, platinum or gold such as ammonium chloropalladate, potassium chloroplatinate, potassium chloropalladite or potassium chlorolaurate. They may contain special sensitisers such as sulphur compounds, tin(II) salts, polyamines or polyalkylene oxide compounds. The emulsions may also be optically sensitised with cyanine dyes, merocyanine dyes or mixed cyanine dyes. Lastly, the emulsions may contain various couplers, e.g. colourless couplers, coloured couplers or couplers which release development inhibitors, stabilisers such as mercury compounds, triazole compounds, azaindene compounds, benzothiazolium compounds or zinc compounds, wetting agents such as dihydroxyalkanes, substances which improve the film-forming properties, for example water-dispersible particulate high polymers obtained by emulsion polymerisation of copolymers of alkylacrylate or alkylmethacrylate with acrylic or methacrylic acid; also styrene/maleic acid copolymers and styrene/maleic acid anhydride semialkyl ester copolymers, coating agents such as polyethylene glycol lauryl ether and various other photograhic additives.

The layers may also contain other hydrophilic colloids in addition to gelatine, i.e. colloidal albumen, agar-agar, gum arabic, dextrans, alginic acid, cellulose derivatives e.g. cellulose acetate which has been hydrolysed up to an acetyl content of 19 to 26%, polyacrylamides, imidatised polyacrylamides, zein, vinyl alcohol polymers containing urethane/carboxylic acid groups or cyanoacetyl groups such as vinyl alcohol-vinyl cyanoacetate copolymers, polyvinyl alcohols, polyvinyl pyrrolidones, hydrolysed polyvinyl acetates, polymers of the kind obtained by polymerisation of proteins or saturated acylated proteins with monomers containing vinyl groups, polyvinylpyridines,, polyvinylamines, polyaminoethylmethacrylates and polyethyleneimines.

The concentrations in which the hardeners according to the invention are used may vary within wide limits and depend mainly on the particular hardening compound used.

Satisfactory results are obtained generally with quantities of from 0.1 to 10% by weight and preferably from 0.2 to 8% by weight, based on the dry weight of binder.

As already mentioned above, the hardening reaction between the compounds according to the invention and gelatine or other protein sets in immediately so that the optimum degree of hardening is obtained simultaneously with the drying of the layers after they have been cast or processed.

The effect of the hardening compound is determined by means of the melting point of the layers, which is measured as follows:

The layer cast on the support is half dipped in water which is continuously heated up to 100° C. The temperature at which the layer runs off its support (formation of streaks) is termed the melting point or melting-off point. By this method of measurement, pure protein or gelatine layers free from hardeners never show any increase in melting point. The melting-off point under these conditions is between 30° and 35° C.

The compounds according to the invention react surprisingly rapidly with proteins so that materials containing protein can be hardened to an optimum degree within a very short time. This unexpected effect of the compounds is particularly important for hardening photographic materials which contain proteins as binder. The desired degree of hardening can be accurately adjusted in practice while preparing the materials and does not require prolonged storage times with the attendant uncertainties of uncontrollable after-hardening. The compounds used according to the present invention are further distinguished by the excellent stability of their aqueous solutions. One effect of this property, for example, is that it enables stock solutions containing the hardeners used according to the invention to be stored for some time without loss of activity of the compounds. This is particularly advantageous in cases where it is necessary to interrupt the casting process when preparing the hardened photographic material. In that case, any reduction in the loss of activity of the hardener in the stock solution would cause uncontrollable changes in the hardening properties of the photographic material.

The invention will now be further explained with the aid of the following Examples in which percentages denote percentages by weight unless otherwise indicated.

EXAMPLE 1

Sodium sulphate was added to a 5% aqueous solution of each of compounds 1 to 15 almost to saturation point. Unhardened photographic silver halide gelatine layers were dipped in these solutions for various lengths of time. The temperature was 22° C. The layers were then briefly rinsed and dried and stored at room temperature for 12 hours. The effect of these preliminary baths was ascertained by measuring the layer melting points of the samples.

| Immersion time in minutes | Layer melting points of Samples 1 - 15 in ° C |
| --- | --- |
| 1 | >100° C |
| 2 | >100° C |
| 3 | >100° C |
| untreated sample | 34° C |

When a bath temperature of 40° C was employed, the time of immersion required was shorter and layer melting points above 100° C were obtained after only 45 seconds.

EXAMPLE 2

A 20% solution of zein in an 8:2 mixture of ethanol and water was prepared and applied to the back of a cellulose acetate film. The layer obtained after drying could easily be dissolved in a mixture of ethanol and water.

When parts of the film were bathed for 3 minutes in a solution of 2 g of compounds 1, 2, 3 and 4,
15 g of sodium sulphate, and
80 ml of water and briefly rinsed and then dried in a heating cupboard at 50 to 60° C, the layer obtained in each case was insoluble in all solvents and was effectively cross-linked.

EXAMPLE 3

An unhardened silver halide emulsion containing 10% by weight of gelatine as binder was cast on a triacetyl cellulose support without the addition of a hardener. The layer contained all the usual additives. Samples of the dry layer were coated with 1%, 2% and 3% aqueous solutions of compounds 1, 2, 12, 13 and 16 and dried. The melting points, swelling values and wet scratch resistances of the layers were then determined. The results are summarised in the following Table.

The swelling values were determined gravimetrically after 10 minutes treatment of the layers in distilled water at 22° C and given as percentages.

To determine the wet scratch resistance, a metal tip of specified size was passed over the wet layer and loaded with increasing weights. The wet scratch resistance is given as the weight at which the tip leaves a visible scratch trace on the layer. A large weight corresponds to high wet scratch resistance and hence a high degree of hardening.

| Compound | Layer melting point | Swelling in % | Wet scratch resistance in p |
| --- | --- | --- | --- |
| Compound 1 | | | |
| 1% | | 300 | 650 |
| 2% | 10'100° * | 280 | 750 |
| 3% | | 250 | 850 |
| Compound 2 | | | |
| 1% | | 295 | 750 |
| 2% | 10'100° | 260 | 950 |
| 3% | | 235 | 950 |
| Compound 12 | | | |
| 1% | | 350 | 550 |
| 2% | 10'100° | 280 | 750 |
| 3% | | 260 | 900 |
| Compound 13 | | | |
| 1% | | 320 | 650 |
| 2% | 10'100° * | 250 | 850 |
| 3% | | 230 | 900 |
| Compound 16 | | | |
| 1% | | 360 | 350 |
| 2% | 10'100° | 310 | 450 |

-continued

| Compound | Layer melting point | Swelling in % | Wet scratch resistance in p |
|---|---|---|---|
| 3% not after-treated: | 36° | 280 600 to 800 | 550 <300 |

* The layer did not dissolve in boiling water after 10 minutes.

EXAMPLE 4

This Example shows the surprising stability of the compounds according to the invention compared with that of carbodiimide compounds which are known as hardeners.

The known compound of the following formula was used for comparison:

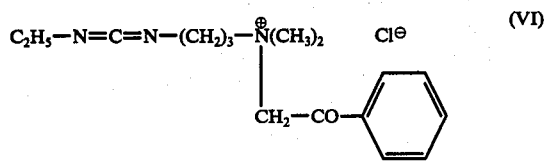
(VI)

and compound 4 of the formula

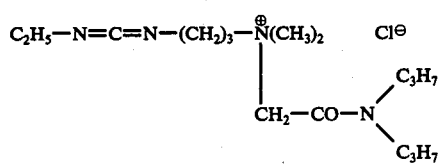

was used to illustrate the invention.

Aqueous casting solutions containing 1/100 mol per 100 cc of Compounds VI and 4, respectively, and 0.375% by weight of saponin as wetting agent were prepared. The solutions were left to digest for 24 hours at 20 C. Before the onset of digestion and after 3, 6 and 24 hours, the activity of the solutions was determined as described in Example 3 by applying a sample to a 10 μ thick silver halide emulsion layer.

The results are summarised in the following Table:

| Digestion time of solution (in hours) | V 1 | | Compound 4 | |
|---|---|---|---|---|
| | Swelling factor in % | Wet scratch resistance 20° C | Swelling factor in % | Wet scratch resistance |
| 0 | 260 | 850 | 280 | 750 |
| 3 | 270 | 750 | 280 | 750 |
| 6 | 290 | 650 | 290 | 750 |
| 24 | 310 | 600 | 280 | 750 |

A comparison of the results shows that the activity of the known compound V 1 changes in the course of digestion while the activity of Compound 4 according to the invention remains practically constant. This property of the compounds according to the invention has considerable advantages, inter alia for the process of preparing photographic materials, since the hardening values of the material are not altered by stoppages of the casting operation.

EXAMPLE 5

20% by weight, based on the quantity of gelatine, of a magenta coupler of the following formula:

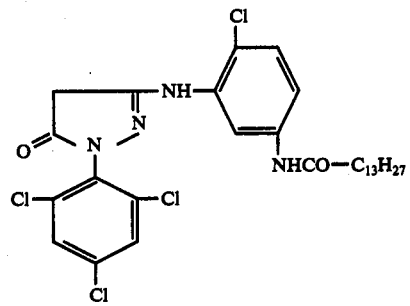

in emulsified form mixed with crystalloid dibutyl phthalate (1:1), were added to an unhardened silver halide emulsion containing 10% by weight of gelatine.

The usual casting additives with the exclusion of a hardener were then added to the emulsion. The mixture was cast on a prepared support of polyethylene terephthalate and dried.

Samples of this layer were then coated with aqueous solutions containing in each case 1/100 mol of one of the compounds indicated below per 100 cc. Exceptionally highly cross-linked layers were obtained after drying and 10 hours storage. The results are shown in the following Tables.

Tables.

| Coating Compound | Melting point | Swelling in % | Wet scratch resistance in p |
|---|---|---|---|
| Compound 1 | 10'100° C | 300 | 750 |
| Compound 2 | 10'100° C | 260 | 950 |
| Compound 6 | 10'100° C | 280 | 750 |
| Compound 9 | 10'100° C | 410 | 250 |
| Compound 13 | 10'100° C | 250 | 850 |
| Compound 16 | 10'100° C | 320 | 450 |
| Treated only with water | 42° C | 800 | — |

The photographic properties were not affected.

EXAMPLE 6

The usual additives with the exclusion of a hardener were added to 100 ml of a photographic silver bromide gelatine emulsion containing 10% by weight of gelatine. The mixture was cast on
 a. baryta paper, and
 b. paper backed with polyethylene on both sides.

After drying, both materials were bathed for 2 minutes in aqueous solutions each containing 3 g of Compounds 1, 2, 5, 10, 11, 12, 13 and 14 in 100 ml of water. The layers obtained after drying and 12 hours storage were in all cases fast to boiling (layer melting points 100° C). The effect of the hardener was not influenced by the support. Layers which had not been after-treated had a melting point of 37° C.

EXAMPLE 7

An unhardened colour photographic multilayered film comprising the following layers was prepared:
1. a 4 μ thick red-sensitive bottom layer containing 35 g of silver bromide, 80 g of gelatine and 24 g if K₁ per kg of emulsion,
2. a 2 μ thick intermediate layer of gelatine,
3. a 4 μ thick green-sensitive middle layer containing 35 g of silver bromide, 80 g of gelatine and 16 g of K₂ per kg of emulsion,
4. a 2 μ thick filter yellow layer of colloidal silver in gelatine, 5. a 4 μ thick blue-sensitive top layer containing 35 g of silver bromide, 80 g of gelatine and 20 g of K₃ per kg of emulsion, and
6. a 2 μ thick protective layer of gelatine.

The following compounds were used as colour couplers:

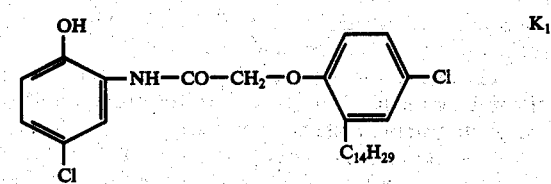

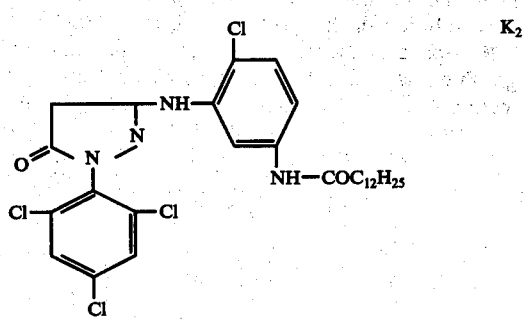

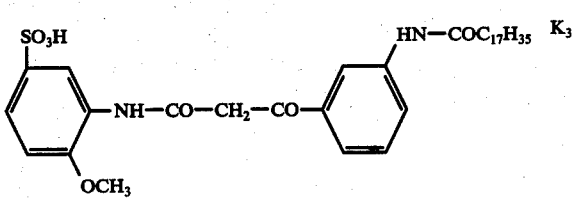

The combination of layers was applied in known manner to a 120 μ thick layer support of cellulose triacetate and dried. Samples of the film were covered with aqueous solutions containing in each case 1/100 mol of one of the compounds 1, 2, 5 and 15 per 100 cc. The layer melting points and the temperatures at which the layers became detached from their supports were determined after drying and 12 hours storage at room temperature.

| Coating compound | Layer detached at | Layer melting point |
|---|---|---|
| Compound 1 | 100° C | 10'100° C |
| Compound 2 | >100° C | 10'100° C |
| Compound 5 | >100° C | 10'100° C |
| Compound 16 | 100° C | 10'100° C |
| Comparison material not coated | 40° C | 40° C |

The results show that the coating effectively cross-linked the multilayered colour photographic castings right down to the lowest layer.

EXAMPLE 8

0.2 g of Compound 1 and of Compound 11 were added in each case to 100 ml of a 10% aqueous solution of acetyl gelatine obtained by reacting gelatine with 20% acetic anhydric, and the mixture was cast on a cellulose acetate film. A layer containing 0.2 g of formalin instead of Compounds 1 and 11 was prepared for comparison. After drying, the layers containing Compounds 1 and 11 were fast to boiling while the layers hardened with formalin melted at temperatures below 100° C.

EXAMPLE 9

This Example demonstrates the greater stability of the compounds according to the invention in aqueous 1% gelatine solutions and 0.2% cellulose sulphate solutions compared with corresponding solutions of known simple aminocarbodiimides.

Solutions of compound 2 and of a carbodiimide of the formula:

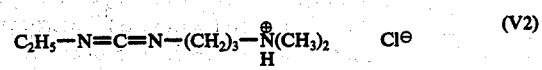

were prepared both in an aqueous 1% by weight gelatine solution and in a 0.2% by weight cellulose sulphate solution, in each case dissolving 1/100 mol of the compound per 100 cc of the gelatine solution or cellulose sulphate solution.

After application to a colour photographic layer containing a coupler, the hardening activities of the solutions were determined as in Example 5 both immediately after preparation of the solutions and after they had been left to stand for 24 hours at 40° C.

a. in 1% gelatine solution

| | Compound V2 | | Compound 2 | |
|---|---|---|---|---|
| Storage time in hours | Swelling at °C % | Wet scratch resistance in p. | Swelling at 20° C % | Wet scratch resistance in p. |
| 0 | 330 | 750 | 280 | 750 |
| 21 | 440 | 550 | 300 | 700 | b. in 0.2% cellulose sulphate solution

| | Compound V2 | | Compound 2 | |
|---|---|---|---|---|
| Storage time in hours | Swelling at 20° C % | Wet scratch resistance in p. | Swelling % | Wet scratch resistance in p. |
| 0 | 290 | 800p | 300 | 750 |
| 24 | 410 | 550p | 350 | 650 |

As the results show, the compounds according to the invention are more stable in the given casting solutions and are distinguished by a more uniform hardening action over 24 hours.

We claim:
1. A process for providing a hardened layer in a photographic material containing a light sensitive silver halide emulsion and at least one layer containing a protein containing binder wherein the improvement comprises incorporating a hardener in the binder which is a water-soluble, organic, asymmetric monocarbadiimide of the formula:

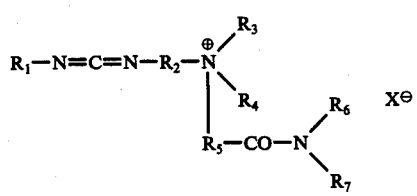

wherein
R₁ denotes alkyl with 1-6 carbon atoms, cycloalkyl, aralkyl, alkoxyalkyl or an olefinically unsaturated lower alkyl group,
R₂ denotes alkylene with 2-4 carbon atoms, $R_3$ and $R_4$ denote alkyl with 1–3 carbon atoms or $R_3$ and $R_4$ together denote the atoms required to complete a 5- to 7-membered saturated heterocyclic ring which may contain other hetero atoms in addition to the nitrogen atom, $R_5$ denotes alkylene with 1 to 3 C-atoms, $R_6$ denotes hydrogen, alkyl with 1 to 4 C-atoms, cycloalkyl, aryl or $SO_2$-alkyl, $R_7$ denotes hydrogen or alkyl with 1 to 9 C-atoms, or $R_6$ and $R_7$ together denote the atoms required to complete a 5- to 7-membered saturated heterocyclic ring which may contain other hetero atoms in addition to the nitrogen atom, and $X^-$ denotes an anion.

2. The process as claimed in claim 1 wherein the binder is comprised of gelatine and homopolymers and copolymers which have carboxyl groups.

3. The process as claimed in claim 1 including the step of applying the hardener from aqueous solution.

4. The process as claimed in claim 1 including the step of applying the hardener from alcoholic solution.

5. The process as claimed in claim 1 including the step of applying the hardener from aqueous alcoholic solution.

6. The process as claimed in claim 1 wherein the layer to be hardened is cast and the hardener is used in quantities of from 0.2 to 8% by weight, based on the weight of the protein-containing binder, in the casting solution for the layer which is to be hardened.

7. The process as claimed in claim 1 including the step of applying the hardener as a 0.1 to 10% solution before the photographic material is processed.

8. The process as claimed in claim 1 wherein the protein-containing binder layer is coated with a 0.1 to 10% solution of the hardener and then dried.

9. A process according to claim 1 wherein the photographic material is a multi-layered color photographic material.

* * * * *

UNITED STATES PATENT AND TRADEMARK OFFICE
CERTIFICATE OF CORRECTION

PATENT NO. : 4,061,499
DATED : December 6, 1977
INVENTOR(S) : HIMMELMANN

It is certified that error appears in the above-identified patent and that said Letters Patent are hereby corrected as shown below:

Column 5, compound 25, right part should read as follows:

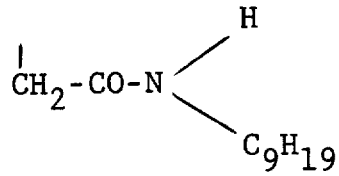

Signed and Sealed this

*Sixteenth* Day of *May 1978*

[SEAL]

Attest:

RUTH C. MASON
Attesting Officer

LUTRELLE F. PARKER
Acting Commissioner of Patents and Trademarks